(12) United States Patent
Hannibal et al.

(10) Patent No.: US 12,233,284 B2
(45) Date of Patent: Feb. 25, 2025

(54) SRS CONTOURED MULTI-LAYER MULTILEAF COLLIMATOR

(71) Applicant: Varian Medical Systems, Inc., Palo Alto, CA (US)

(72) Inventors: Ross B Hannibal, Saratoga, CA (US); Paul Baturin, Santa Clara, CA (US); David Schaal, Sunnyvale, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 965 days.

(21) Appl. No.: 17/195,492

(22) Filed: Mar. 8, 2021

(65) Prior Publication Data

US 2022/0280812 A1 Sep. 8, 2022

(51) Int. Cl.
*A61N 5/10* (2006.01)
*A61B 90/10* (2016.01)
*G21K 1/04* (2006.01)

(52) U.S. Cl.
CPC .......... *A61N 5/1045* (2013.01); *A61N 5/1084* (2013.01)

(58) Field of Classification Search
CPC ............... A61N 5/1045; A61N 5/1084; A61B 2090/101; G21K 1/046
See application file for complete search history.

(56) References Cited

U.S. PATENT DOCUMENTS

| | | | |
|---|---|---|---|
| 8,637,841 B2 | 1/2014 | Prince et al. | |
| 2012/0043482 A1* | 2/2012 | Prince | G21K 1/046 |
| | | | 250/505.1 |
| 2015/0273239 A1* | 10/2015 | Hsu | A61N 5/1045 |
| | | | 378/150 |
| 2017/0197094 A1 | 7/2017 | Popple | |
| 2018/0104511 A1 | 4/2018 | Hsu et al. | |
| 2020/0346037 A1* | 11/2020 | Zankowski | G21K 1/046 |

FOREIGN PATENT DOCUMENTS

GB 2526103 A 11/2015

* cited by examiner

*Primary Examiner* — Thaddeus B Cox
*Assistant Examiner* — Joshua Daryl D Lannu
(74) *Attorney, Agent, or Firm* — Harness, Dickey & Pierce, P.L.C.

(57) ABSTRACT

An apparatus includes a first multileaf collimator comprising a plurality of pairs of beam-blocking leaves each comprising an end portion. The end portions of the beam-blocking leaves of one pair are contoured to allow forming a first aperture when the beam-blocking leaves of the pair are closed. The first aperture has a closed shape such as a circle in a beam's eye view.

18 Claims, 14 Drawing Sheets

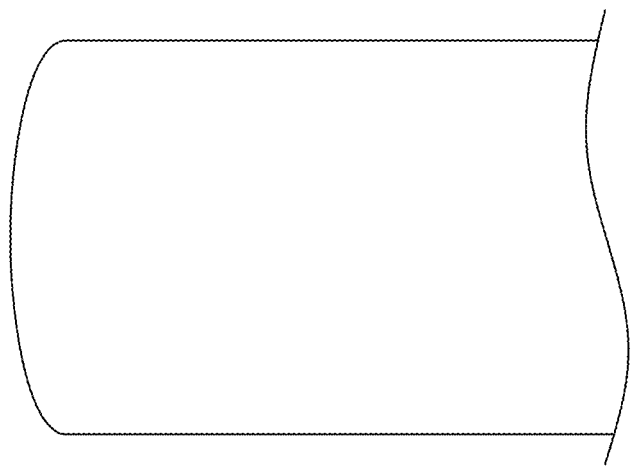
FIG. 2A
   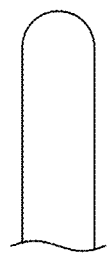   
FIG. 2B     FIG. 2C     FIG. 2D

SRS CONTOURED MULTI-LAYER MULTILEAF COLLIMATOR

TECHNICAL FIELD

This disclosure relates generally to radiation apparatuses and methods. In particular, various embodiments of multileaf collimators (MLCs) enabling and enhancing radiosurgery and stereotactic radiosurgery (SRS) are described.

BACKGROUND

Stereotactic radiosurgery (SRS) is an important modality in radiation therapy to treat brain lesions in adults and children. Conventionally, SRS cones are used to help achieve precise delivery of high dose of radiation. SRS cones are typically made from tungsten and have a conical hole through which radiation can pass providing a focused treatment beam. SRS cones can be mounted externally to an interface mount on a linear accelerator or internally on a positioning device in the treatment head. Inclusion of SRS cones in a treatment head requires more space for installation and complex motion axes. If mounted externally, SRS cones may present potential collision hazard with treatment couch or patient and generally involve compromises in efficiency of treatment delivery.

U.S. Patent Application Publication No. 2017-0197094 discloses a "virtual cone" approach using an MLC. According to the "virtual cone" approach, an MLC is used to form an actual elongated aperture through which radiation is delivered to a target volume at a first orientation of the MLC. Then, the MLC is rotated to a second orientation and radiation is delivered to the target volume through the actual elongated aperture. A relatively large cumulative dose of radiation can be thus delivered to the target volume through a "virtual cone" created by an area of overlap between the actual elongated apertures at the first and second MLC orientations. The "virtual cone" approach requires double passes of an MLC per couch angle and the general MLC leaf shape designed for other purposes may result in compromises in the shape of delivered radiation and may cause concerns of users that it may not produce robust implementation of radiation delivery.

Multi-layer MLCs have advantages of low intra-leaf and inter-leaf leakage, or low out-of-field-dose, compared to conventional single-layer MLCs. This is particularly useful for pediatric patients where dose to normal tissue needs to be minimized. Pediatric patients have a disproportionately larger number of cranial lesions compared to adults. However, multi-layer MLCs usually have larger leaf widths compared to conventional single-layer MLCs. While multi-layer MLCs can generally handle larger field sizes quickly and accurately, they have difficulties in achieving adequate dose distribution in field shaping and dose fall-off for small field sizes required for SRS.

Therefore, there is a general need for MLCs which can be used for both SRS and standard radiotherapy for both pediatric and adult patients. It would be desirable to create multi-layer MLCs which can provide multiple field sizes for SRS of targets of varying sizes and shapes.

SUMMARY

An embodiment of the disclosure provides an apparatus comprising a first multileaf collimator. The first multileaf collimator comprises a plurality of pairs of beam-blocking leaves each comprising an end portion, wherein the end portions of the beam-blocking leaves of one pair are contoured to allow forming a first aperture when the beam-blocking leaves of the pair are closed. The first aperture has a closed shape in a beam's eye view.

This Summary is provided to introduce selected aspects and embodiments of this disclosure in a simplified form and is not intended to identify key features or essential characteristics of the claimed subject matter, nor is it intended to be used as an aid in determining the scope of the claimed subject matter. The selected aspects and embodiments are presented merely to provide the reader with a brief summary of certain forms the invention might take and are not intended to limit the scope of the invention. Other aspects and embodiments of the disclosure are described in the section of Detailed Description.

BRIEF DESCRIPTION OF THE DRAWINGS

These and various other features and advantages will become better understood upon reading of the following detailed description in conjunction with the accompanying drawings provided below, where:

FIGS. 2A-2D depict example leaf tip profiles according to embodiments of the disclosure. FIG. 2A is a side view of an example beam-blocking leaf. FIG. 2B is a top view of an example beam-blocking leaf. FIG. 2C is a top view of another example beam-blocking leaf. FIG. 2D is a top view of a further example beam-blocking leaf.

FIG. 5A is a beam's eye view showing the leaf tip profile. FIG. 5B is a side view showing the leaf tip profile.

FIG. 6A is a beam's eye view showing the beam-blocking leaves of two adjacent pairs when opened or retracted. FIG. 6B is a beam's eye view showing a circular aperture formed by the beam-blocking leaves of the two adjacent pairs when closed.

FIG. 7A is a beam's eye view showing the beam-blocking leaves of two adjacent pairs when opened or retracted. FIG. 7B is a beam's eye view showing a square-shaped aperture formed by the beam-blocking leaves of the two adjacent pairs when closed.

FIG. 8A is a beam's eye view of the multi-layer MLC in use for SRS. FIG. 8B is a side view of a pair of beam-blocking leaves, taken along line A-A in FIG. 8A. FIG. 8C is a beam's eye view showing an aperture formed by a pair of beam-blocking leaves in a distal layer of the multi-layer MLC. FIG. 8D is a beam's eye view of the multi-layer MLC not in use for SRS or in use for a standard treatment.

FIG. 9A is an isometric view showing the leaf tip profile. FIG. 9B is a beam's eye view showing an aperture formed by two adjacent pairs of beam-blocking leaves having a leaf tip profile similar to that shown in FIG. 9A. FIG. 9C is a side view showing effect of the example beam-blocking leaves on shading radiation in a standard treatment.

FIG. 10A is a bottom view of the multi-layer MLC. FIG. 10B is a bottom view of a pair of beam-blocking leaves in the proximal layer of the multi-layer MLC.

DETAILED DESCRIPTION OF EMBODIMENTS

With reference to FIGS. 1-13, various embodiments of multileaf collimators (MLCs) and methods will be described. It should be noted that the figures are intended for illustration of embodiments but not as an exhaustive description or a limitation on the scope of the disclosure. Alternative embodiments of the structures and methods shown and described herein will be readily recognized as being viable without departing from the principle of the claimed invention.

In general, the disclosure provides solutions for stereotactic radiosurgery (SRS) and radiosurgery using specially designed MLCs. One solution is to contour or shape the leaf tips of selected beam-blocking leaves of a multi-layer MLC to allow forming a small aperture when the selected beam-blocking leaves are closed. The small aperture allows a thin beam to pass through, creating a focused treatment field accurately conforming to a target to be treated. The disclosed approach allows delivery of small SRS cone-like beam profiles directly from a multi-layer MLC, enabling high resolution treatments for difficult-to-treat cranial lesions while fully preserving the general purpose or functionality of the multi-layer MLC and maintaining the advantages of the multi-layer MLC such as compactness, excellent shielding, and ample room for large robust drivetrain.

Figure 1:
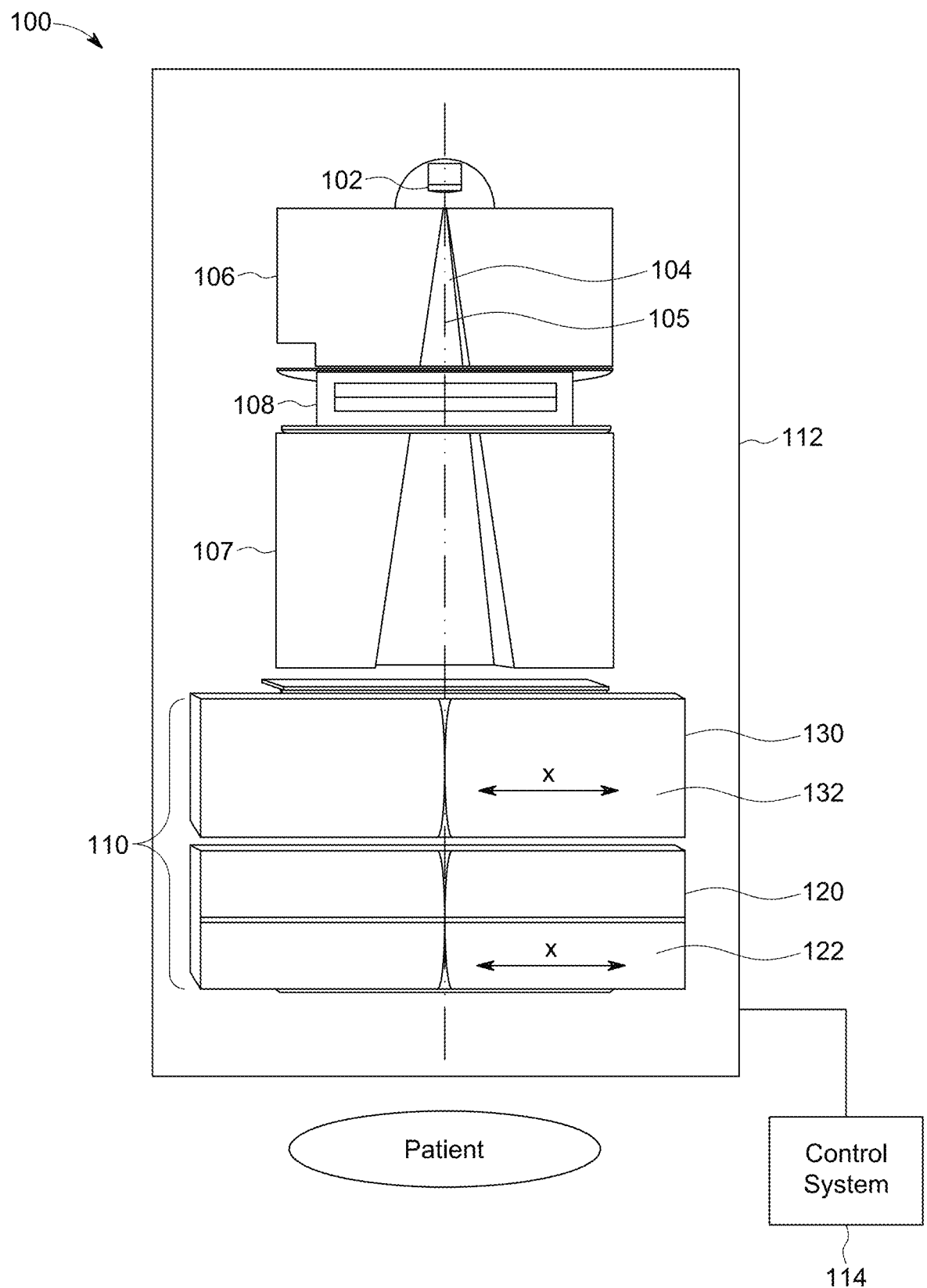
FIG. 1 is a simplified illustration of a radiation apparatus including an example multi-layer multileaf collimator (MLC) according to embodiments of the disclosure.

With reference to FIG. 1, a radiation system or apparatus 100 includes an MLC 110 according to embodiments of the disclosure. As shown, the radiation apparatus 100 comprises a radiation source 102 producing or emitting a beam 104 of radiation such as photons, electrons, protons, or other types of radiation. By way of example, the radiation source 102 may include a metallic target configured to produce a beam of photons or x-rays upon impingement of electrons.

The radiation apparatus 100 may also include various collimating devices or components configured to limit, define, or modify the size, shape, fluence, and other characteristics of the beam 104. For example, a primary collimator 106 adjacent to the source 102 and optionally a secondary collimator 107 may generally limit the extent of the divergent beam 104 as it travels away from the source 102. The beam's central axis 105, an axis passing through the source 102 and perpendicular to an isocenter plane, may be used to indicate the beam propagation direction and describe various components as viewed from the source 102. An ion chamber 108 may be disposed in the beam path to monitor the characteristics of the beam 104.

The MLC 110 can be disposed between the source 102 and a patient to further shape and size the beam 104. The MLC 110 may be rotated about the beam's central axis 105, allowing the MLC 110 to be placed in various orientations relative to the patient. The source 102, primary collimator 106, secondary collimator 107, ion chamber 108, MLC 110, and other devices or components may be enclosed in a treatment head 112, which can be rotated by a gantry, such as a ring gantry or a C-arm gantry, about an axis such as a horizontal axis, or moved by a robotic arm. Therefore, the apparatus 100 can deliver radiation to a target in the patient from various angles. The shape, size, and/or intensity of the beam 104 can be adjusted, or dynamically adjusted, by the MLC 110 as the beam angle is stepped or swept around the target. The operation of the source 102, MLC 110, and other devices can be controlled by a control system 114.

With reference to FIG. 1, the MLC 110 may be a multi-layer MLC as shown. Alternatively, the MLC 110 may be a single-layer MLC. By way of example, the multi-layer MLC 110 may include a first layer 120 distal to the source 102 and a second layer 130 proximal to the source 102. In describing various embodiments of the disclosure, the terms "first layer" and "second layer" of a multi-layer MLC may be used interchangeably with the terms "first MLC in a first level" or "second MLC in a second level." The multi-layer MLC 110 may be constructed as a single unit including a first MLC 120 and a second MLC 130. Alternatively, the first MLC 120 and the second MLC 130 may be separately constructed and disposed or positioned relative to each other in the treatment head 112. As used herein, the term "MLC" or "multileaf collimator" refers to a collection of a plurality of beam-blocking leaves each of which can be longitudinally moved in and out of a beam path to modify one or more characteristics of the beam such as the beam shape, size, energy, or intensity etc. Each beam-blocking leaf may be driven by a motor with a lead screw or other suitable means. The beam-blocking leaves may be arranged in pairs. The beam-blocking leaves of each pair may be brought in contact or retracted from each other to close or open a path for a beam to pass through. The beam-blocking leaves may be arranged in opposing banks and supported by a supporting structure such as a frame, box, carriage or the like, which has features allowing the individual beam-blocking leaves to extend into and retract from the beam path. The supporting structure such as a frame, box, carriage or the like can be further translated or moved in addition to the individual leaf travel.

With reference to FIG. 1, the first MLC 120 and the second MLC 130 may be arranged such that the moving direction of beam-blocking leaves 122 of the first MLC 120 and the moving direction of the beam-blocking leaves 132 of the second MLC 130 are generally in parallel. For example, as shown in FIG. 1, the beam-blocking leaves 122 of the first MLC 120 in the first level are longitudinally movable in the x-direction, and the beam-blocking leaves 132 of the second MLC 130 in the second level are also longitudinally movable in the x-direction. Alternatively, the first MLC 120 and the second MLC 130 may be arranged such that the moving direction of the beam-blocking leaves 122 of the first MLC 120 is non-parallel with e.g., perpendicular to the moving direction of the beam-blocking leaves 132 of the second MLC 130.

Figure 2:
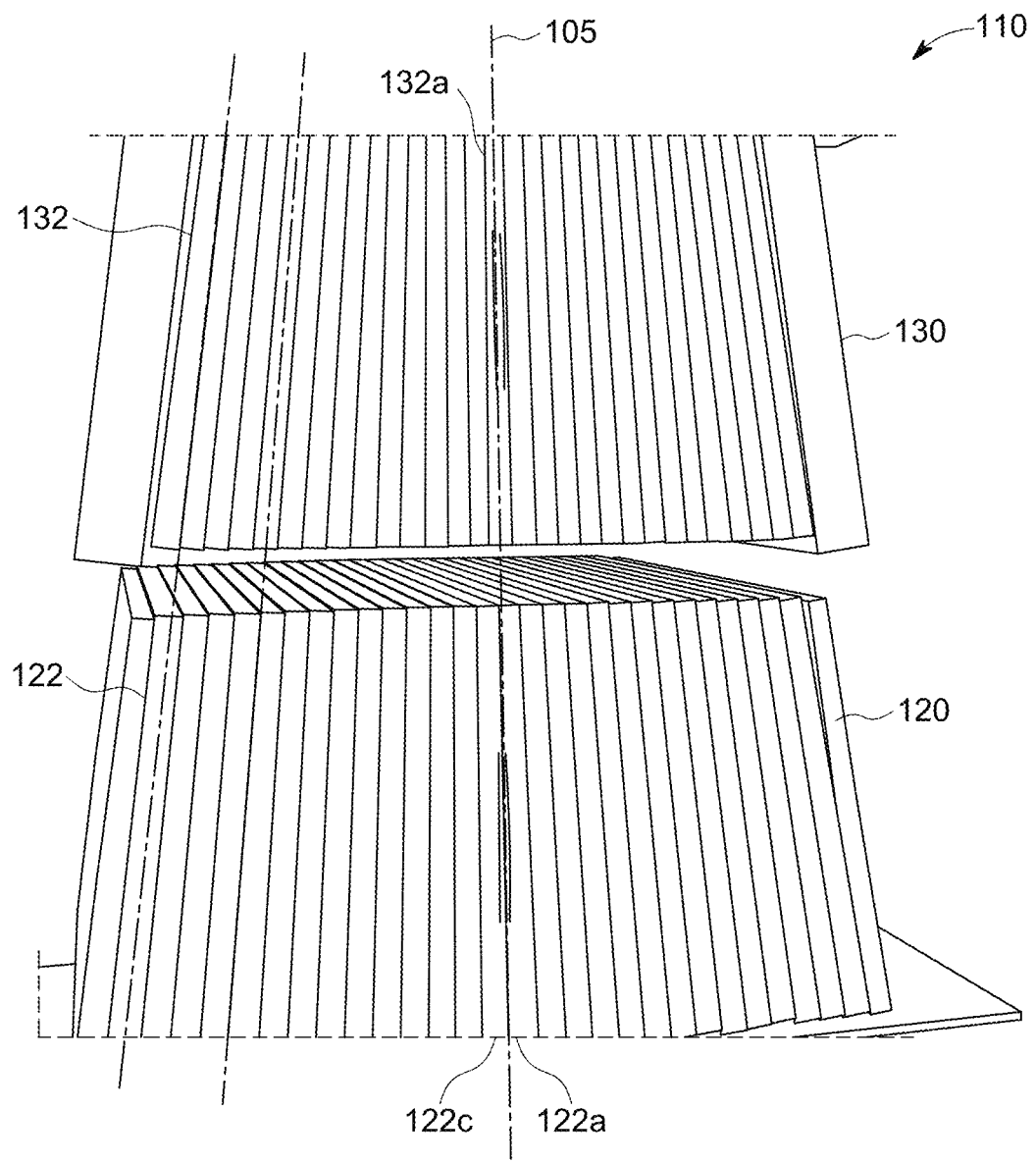
FIG. 2 is a cross-sectional view of the multi-layer MLC shown in FIG. 1, taken along a central line of the multi-layer MLC.

With reference to FIG. 2, the first MLC 120 and the second MLC 130 may be arranged such that the beam-blocking leaves 132 of the second MLC 130 laterally offset the beam-blocking leaves 122 of the first MLC 120 in the beam's eye view, or as viewed in a direction from the source 102. FIG. 2 is a cross-sectional view of the multi-layer MLC 110 of FIG. 1, taken along a central line of the multi-layer MLC 110, showing the lateral offset arrangement of the beam-blocking leaves of the multi-layer MLC 110. As shown, a beam-blocking leaf 132 of the second MLC 130 in the second level offsets a beam-blocking leaf 122 of the first MLC 120 in the first level, as viewed from the source 102. By way of example, a beam-blocking leaf 132 of the second MLC 130 may offset a beam-blocking leaf 122 of the first MLC 120 by substantially half a leaf width. Alternatively, a gap between two adjacent beam-blocking leaves 132 of the second MLC 130 in the second level may be positioned substantially at the middle of a beam-blocking leaf 122 of the first MLC 120. The lateral offset arrangement of beam-blocking leaves in different levels can help reduce intra-leaf and inter-leaf leakage. The lateral offset arrangement of beam-blocking leaves in different levels also provides for leaf projections that are offset at the isocenter plane. Therefore, the lateral offset arrangement of beam-blocking leaves can also provide for substantially an equivalent of doubling MLC definition, or improving the resolution to half as compared to the definition of a single-layer MLC with beam-blocking leaves of the same physical width. In some embodiments, three or more MLCs may be arranged in three or more levels such that each beam-blocking leaf at a level may offset e.g., by ⅓ or 1/n of a leaf width as projected at the isocenter plane where n is the number of the MLCs. U.S. Pat. No. 8,637,841 issued on Jan. 28, 2014 to the common assignee entitled "Multi Level Multileaf Collimators" describes various embodiments of multi-level MLCs, the disclosure of which is incorporated herein by reference in its entirety.

With reference to FIG. 2, the beam-blocking leaves 122 of the first MLC 120 and the beam-blocking leaves 132 of the second MLC 130 may have various leaf tip profiles or end portion configurations. For ease of description of the leaf tip profiles and the MLC 110 in general, the term "top view" may be used interchangeably with the term "beam's eye view" to refer to a view observed from the source or in a direction parallel to the beam's central axis. The term "bottom view" may be used to refer to a view opposite to the top view. The term "side view" may be used to describe a view observed from a side surface of a beam-blocking leaf.

In some embodiments, the beam-blocking leaves 122, 132 of the multi-layer MLC 110 may have a rounded front-end surface. In a side view, a beam-blocking leaf with a rounded front-end surface may be shown to have a curved line and two parallel lines at either end of the curved line, as shown in FIG. 2A. The rounded front-end surface may be machined so that in a top view, the rounded front-end surface or a cross-section of the rounded front-end surface may be shown to have a straight line orthogonal to the leaf longitudinal moving direction, as shown in FIG. 2B. The rounded front-end surface may also be machined or contoured so that in a top view, the rounded front-end surface or a cross-section of the rounded front-end surface may be shown to have a curved line, as shown in FIG. 2C, or a combination of straight lines, as shown in FIG. 2D. For example, a chamfer leaf may have a leaf tip profile or a leaf end portion which includes a rounded front-end surface and one or two beveled surfaces on one or either side of the rounded front-end surface. Therefore, a cross-section of a chamfer leaf in a side view may be shown to have a curved line and two parallel lines at either end of the curved line, as shown in FIG. 2A. In a top view, a cross-section of a chamfer leaf may be shown to have a combination of a straight line orthogonal to the leaf longitudinal moving direction and one or two beveled lines at one or either end of the straight line, as shown in FIG. 2D. In alternative embodiments, the beam-blocking leaves 122, 132 of the multi-layer MLC 110 may have a flat front-end surface. In both a side view and a beam's eye view, a beam-blocking leaf with a flat front-end surface may be shown to have a straight line orthogonal to the leaf longitudinal moving direction.

Figure 3:
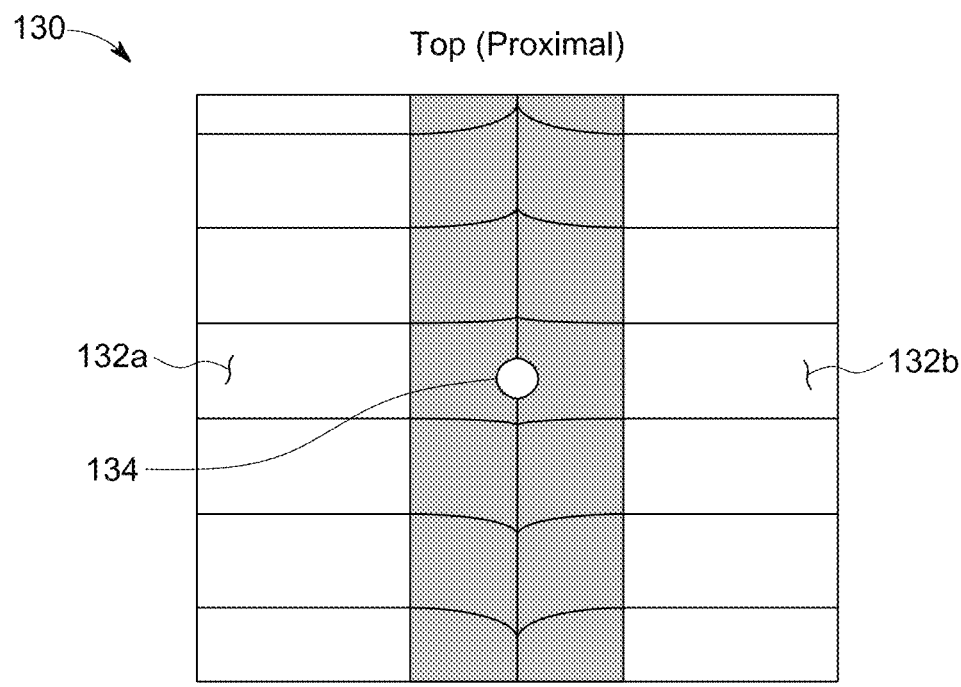
FIG. 3 is a beam's eye view of a proximal layer of the multi-layer MLC shown in FIG. 1.

According to embodiments of the disclosure, two opposing beam-blocking leaves of a selected pair in an MLC may include a contoured end surface or end portion that allows forming a small aperture when the selected pair of beam-blocking leaves are closed. As such, when all beam-blocking leaves of the MLC are closed, the two opposing leaves of the selected pair form a small aperture, allowing a thin beam to pass through to enable SRS or radiosurgery. FIG. 3 is a beam's eye view of an example MLC or a layer of a multi-layer MLC, showing an aperture formed by two opposing beam-blocking leaves of a selected pair. By way of example, the proximal layer 130 of the multi-layer MLC 110 shown in FIG. 2 may include a pair of beam-blocking leaves 132a, 132b, which can form an aperture 134 when the pair of beam-blocking leaves 132a, 132b are closed. The aperture 134 is shown to have a closed shape in the beam's eye view. In FIG. 3, the closed shape is in the form of a circle. Other closed shapes such as oval, oblong, square, and other regular or irregular shapes are possible and anticipated by the inventors.

Figure 4:
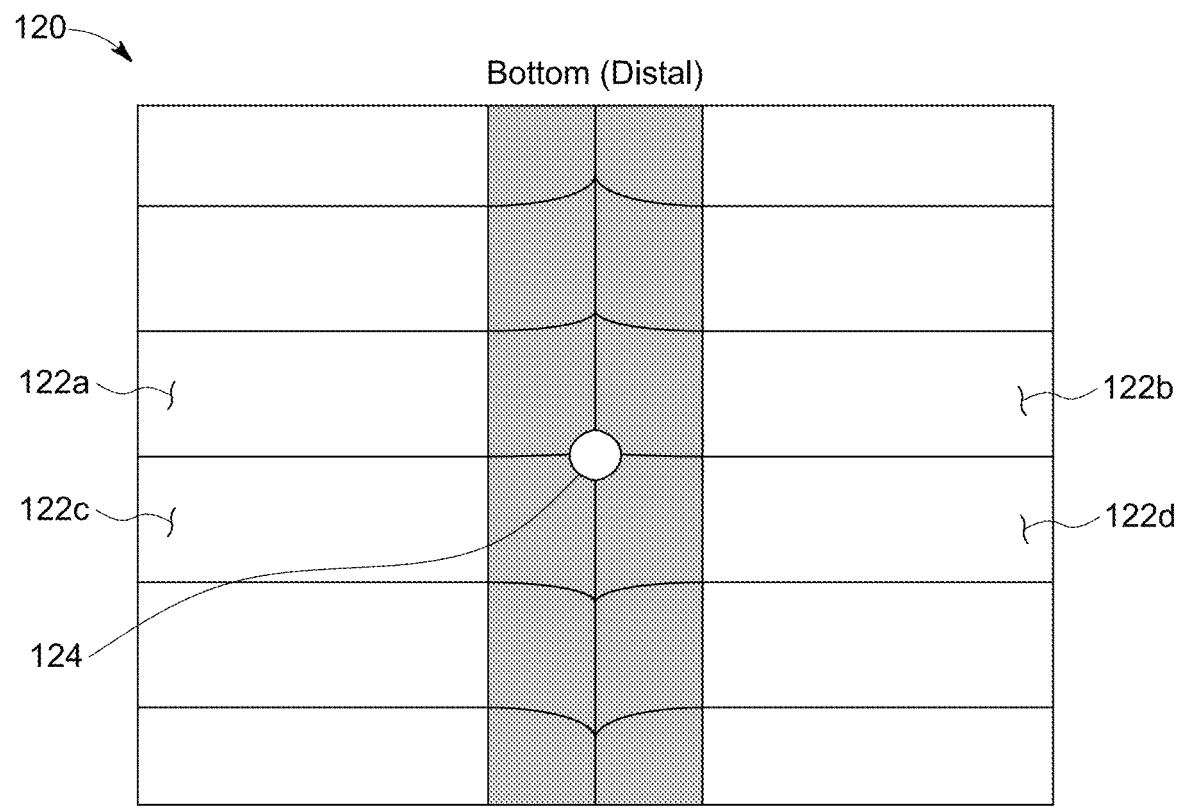
FIG. 4 is a beam's eye view of a distal layer of the multi-layer MLC shown in FIG. 1.

According to embodiments of the disclosure, four opposing beam-blocking leaves of two adjacent pairs in an MLC may include a contoured end surface or end portion that allows forming a small aperture when the two adjacent pairs of beam-blocking leaves are closed. As such, when all beam-blocking leaves of the MLC are closed, the four beam-blocking leaves of the two adjacent pairs form a small aperture, allowing a thin beam to pass through for SRS or radiosurgery. FIG. 4 is beam's eye view of an example MLC or a layer of a multi-layer MLC, showing an aperture formed by four opposing beam-blocking leaves of two adjacent pairs. By way of example, the distal layer 120 of the multi-layer MLC 110 of FIGS. 2 and 4 may include two adjacent pairs of beam-blocking leaves 122a-122b and 122c-122d, which can form an aperture 124 when the two adjacent pairs of beam-blocking leaves 122a-122b and 122c-122d are closed. The aperture 124 is shown to have a closed shape in the beam's eye view. In FIG. 4, the closed shape is in the form of a circle. Other closed shapes such as oval, oblong, square, and other regular or irregular shapes are possible and anticipated by the inventors.

According to embodiments of the disclosure, a multi-layer MLC comprises a first MLC in a first level and a second MLC in a second level. The first MLC may include a pair of beam-blocking leaves each having a leaf end portion contoured or shaped to allow forming a small aperture when the pair of beam-blocking leaves are closed. The second MLC may include two adjacent pairs of beam-blocking leaves each having a leaf end portion contoured or shaped to allow forming a small aperture when the two adjacent pairs of beam-blocking leaves are closed. In use for SRS, all of the beam-blocking leaves of the multi-layer MLC may be closed. The aperture formed by the pair of beam-blocking leaves in the first MLC can be aligned with the aperture formed by the two adjacent pairs of the beam-blocking leaves in the second MLC, allowing a thin beam to pass through the multi-layer MLC for SRS or radiosurgery. FIG. 2 shows a multi-layer MLC 110 including a proximal layer 130 having a pair of beam-blocking leaves each having a contoured end portion (showing only leaf 132a in FIG. 2), and a distal layer 120 having two adjacent pairs of beam-blocking leaves each having a contoured end portion (showing only leaf 122a and 122c in FIG. 2). In FIGS. 2 and 4, the pair of beam-blocking leaves 132a, 132b in the proximal layer 130 and the two adjacent pairs of beam-blocking leaves 122a-122b and 122c-122d in the distal layer 120 are shown to be disposed in the middle of the multi-layer MLC 110. Such arrangement may facilitate alignment of the aperture formed in the multi-layer MLC 110 with the beam's central axis 105 when in use. Alternatively, the pair of beam-blocking leaves 132a-132b and the two adjacent pairs of beam-blocking leaves 122a-122b and 122c-122d can be disposed off-center of the multi-layer MLC 110. The alignment the aperture formed in the multi-layer MLC 100 with the target can also be achieved by moving the supporting structure of the multi-layer MLC or by moving the patient support or couch. Further, it should be noted that the pair of beam-blocking leaves 132a-132b having a contoured end portion can be alternatively disposed in the distal layer, and the two adjacent pairs of beam-blocking leaves 122a-122b and 122c-122d having a contoured end portion can be alternatively disposed in the proximal layer.

Figure 5A:
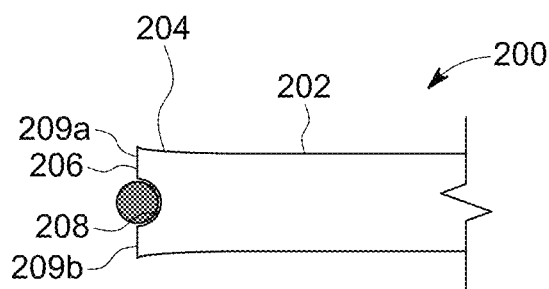
FIGS. 5A-5B depict an example beam-blocking leaf according to embodiments of the disclosure.
Figure 5B:
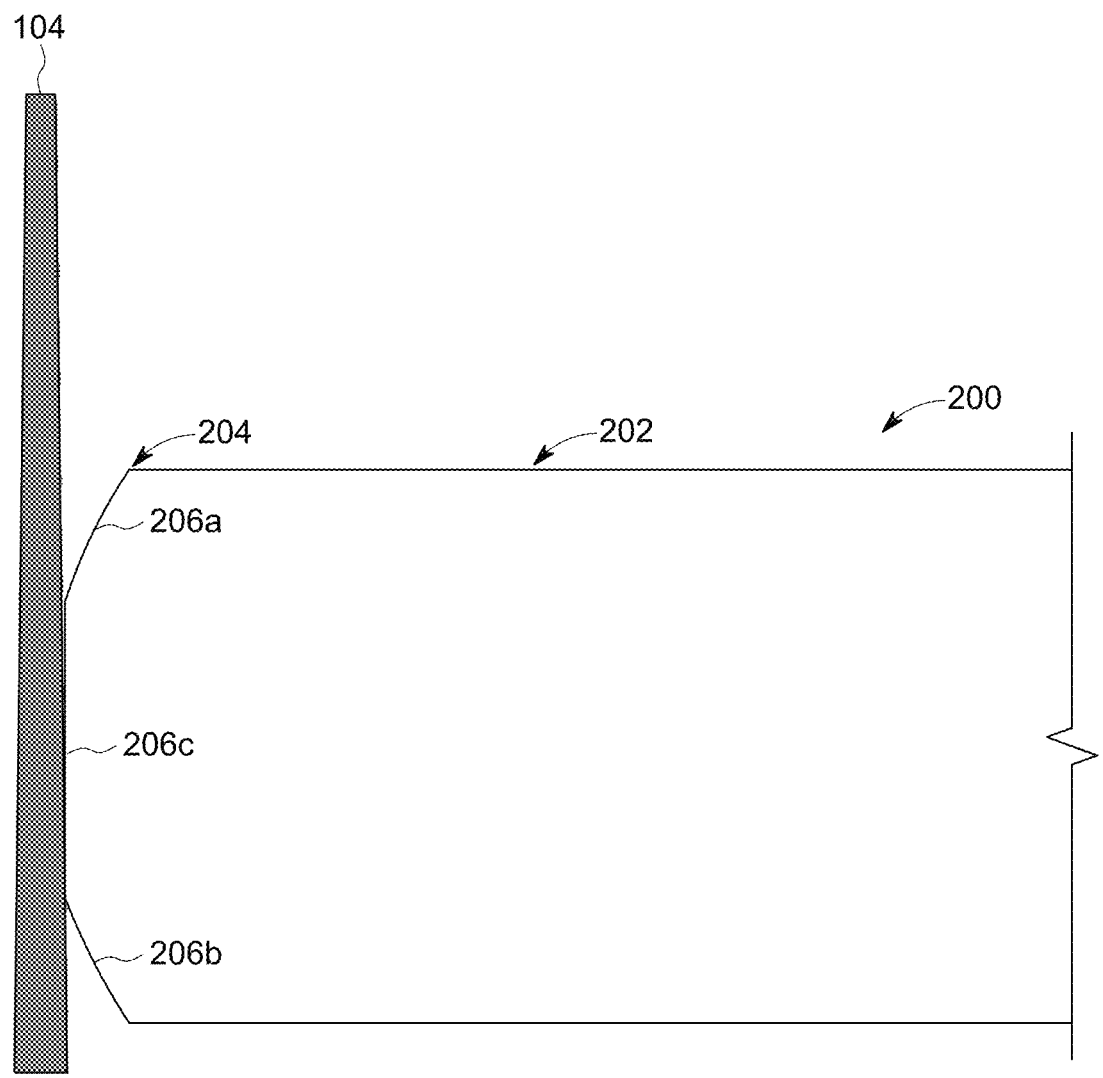

With reference now to FIGS. 5A-5B, according to embodiments of the disclosure, the end portion of two opposing beam-blocking leaves of a pair in an MLC can be contoured or shaped to allow forming a small aperture when the pair of beam-blocking leaves are closed. FIG. 5A is a beam's eye view showing the profile of the end portion of an example beam-blocking leaf 200. FIG. 5B is a side view of the example beam-blocking leaf 200. As shown, the example beam-blocking leaf 200 includes a main body portion 202 and an end portion 204. The end portion 204 comprises a front-end surface, or an end surface 206 extending the height of the leaf main body portion 202. According to embodiments of the disclosure, the end surface 206 of the beam-blocking leaf 200 includes a concaved surface portion 208, configured to allow forming an aperture when two opposing beam-blocking leaves having the leaf tip profile shown in FIGS. 5A-5B are brought in contact. The concaved surface portion 208 may extend from the top to the bottom of the leaf body portion 202 or partially extend the height of the body portion 202.

With reference to FIGS. 5A-5B, according to a particular embodiment, the concaved surface portion 208 in the end surface 206 of the beam-blocking leaf 200, or a cross-section of the concaved surface portion 208, has the shape of a semi-circle in the beam's eye view. In an MLC or multi-layer MLC, two beam-blocking leaves 200 having a leaf tip profile shown in FIGS. 5A-5B may be paired. As such, when the pair of two opposing beam-blocking leaves 200 are brought in contact, an aperture can be formed by the concaved surface portions 208 of two opposing beam-blocking leaves 200. The concaved surface portions 208 may be machined or contoured so that the aperture formed is generally in a cylindrical shape. The concaved surface portions 208 may also be machined or contoured so that the aperture formed is generally in a truncated cone shape. In the beam's eye view, the aperture or a cross-section of the aperture has the shape of a circle. Other regular or irregular concaved surface portions can be readily machined, and are anticipated by the inventors.

With reference to FIGS. 5A-5B, according to some embodiments of the disclosure, the front-end surface 206 of the beam-blocking leaf 200 may include a rounded section or sections, for example, a first rounded section 206a starting at the top of the main body portion 202 and a second rounded section 206b starting at the bottom of the main body portion 202. In some embodiments, the front-end surface 206 of the beam-blocking leaf 200 may include a third section 206c between the first rounded section 206a and the second rounded section 206b. The third section 206c may be sculpted, carved, or configured to include a concaved surface portion 208 which allows to form an aperture when two opposing beam-blocking leaves 200 are brought in contact.

In some embodiments, the third section 206c may further include one or two flat surface portions 209a, 209b on one or either side of the concaved surface portion 208. The flat surface portion or portions 209a, 209b can provide an increased contact surface when two opposing beam-blocking leaves 200 are brought in contact to form an aperture, which in turn can improve the performance of the MLC e.g., reducing leakage or improving penumbra. Alternatively, the third section 206c may include one or two rounded surface portions, forming a continuous rounded end surface with the first and second rounded sections 206a, 206b.

With reference to FIGS. 5A-5B, the concaved surface portion 208 may be machined or contoured so that the aperture formed by two opposing beam-blocking leaves 200 has a size capable of creating a treatment field at the isocenter plane with a field size suitable for stereotactic radiosurgery. By way of example, the concaved surface portion 208 may be machined to allow forming an aperture having a diameter e.g., ranging from 1-10 mm, or providing a field size at the isocenter plane e.g., ranging from 2 to 15 millimeters, 4 to 8 millimeters, 5-6 millimeters, or other dimensions generally suitable for stereotactic radiosurgery. As used herein, the term "about" includes variances within 1 millimeter of the size referred to. The concaved surface portion 208 may be machined so that the aperture formed may have a size about a third or a half of the thickness of leaf body. The concaved surface portion 208 may be machined in or approximately in the middle of the beam-blocking leaf 200.

Figure 6A:
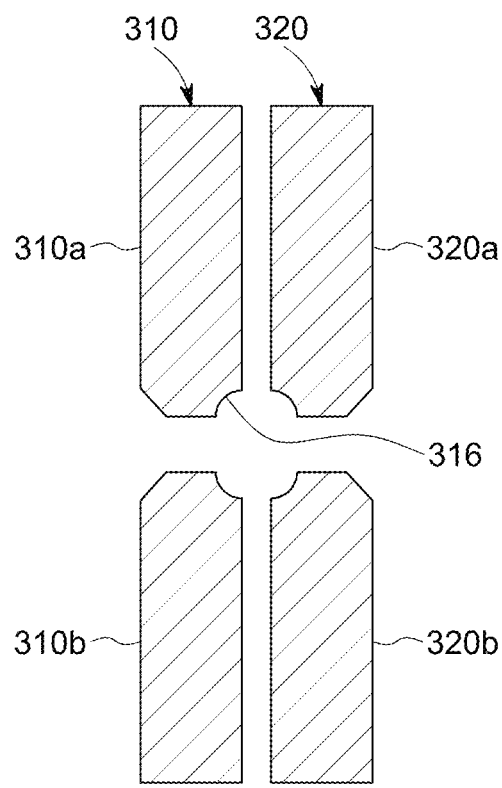
FIGS. 6A-6B depict example beam-blocking leaves according to embodiments of the disclosure.
Figure 6B:
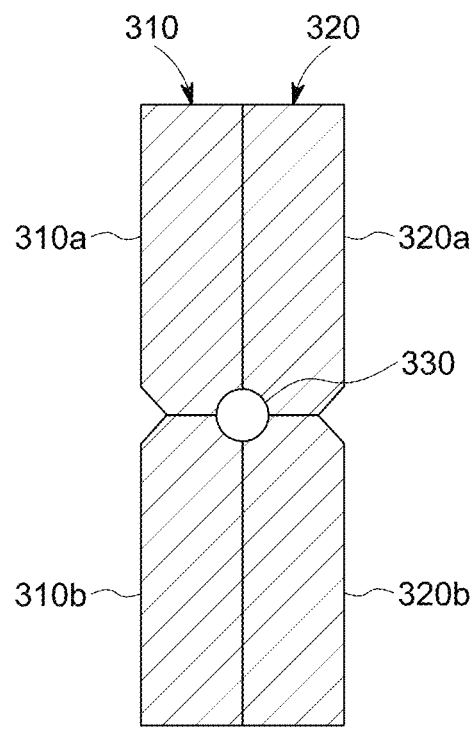

With reference now to FIGS. 6A-6B, according to embodiments of the disclosure, four opposing beam-blocking leaves of two adjacent pairs may each have an end portion contoured to allow forming a small aperture when the two adjacent pairs of beam-blocking leaves are closed. FIG. 6A shows two adjacent pairs 310 and 320 of beam-blocking leaves 310a-310b and 320a-320b when the leaves of each pair are retracted or opened. The gap between the sides of the adjacent beam-blocking leaves 310a and 320a or 310b and 320b is exaggerated for purpose of illustrating the leaf tip profiles with greater clarity. FIG. 6B shows the two adjacent pairs 310 and 320 of the beam-blocking leaves 310a-310b and 320a-320b when brought into contact or closed, forming an aperture 330. As shown, the leaf end portions of the beam-blocking leaves 310a-310b and 320a-320b may be configured such that an aperture having a generally truncated cone shape or cylindrical shape or an equivalent of truncated cone or cylindrical shape is formed when the beam-blocking leaves 310a-310b and 320a-320b are closed. In the beam's eye view, the aperture 330 or a cross-section of the aperture 330 may be shown to have a circular shape.

By way of example, the beam-blocking leaf 310a of the pair 310 may have a leaf end portion including a concaved surface portion, extending from the top to the bottom of the beam-blocking leaf 310a or partially extending the height of the beam-blocking leaf 310a. In a beam's eye view, the concaved surface portion or a cross-section of the concaved surface portion will be shown to have a curved line 316, as shown in FIG. 6A. In a specific embodiment shown in FIG. 6A, the curved line section 316 may be in the shape of a quarter-circle. The beam-blocking leaf 310b of the pair 310 may have a leaf tip profile that is a mirror image of the leaf tip profile of the opposing beam-blocking leaf 310a. Therefore, when the beam-blocking leaves 310a, 310b of the pair 310 are closed, a semi-circle line can be formed by the quarter-circle lines of the beam-blocking leaves 310a and 310b, as shown in FIG. 6B. Likewise, the beam-blocking leaf 320a of the adjacent pair 320 may have a leaf end portion that is a mirror image of the leaf tip profile of the opposing beam-blocking leaf 320b so that when the beam-blocking leaves 320a, 320b of the pair 320 are closed, a semi-circle line is formed by the quarter-circle lines of beam-blocking leaves 320a and 320b. When the two adjacent pairs 310 and 320 of the four beam-blocking leaves 310a-310b and 320a-320b are closed, a circle 330 is formed by the quarter-circle lines of the beam-blocking leaves.

Figure 7A:
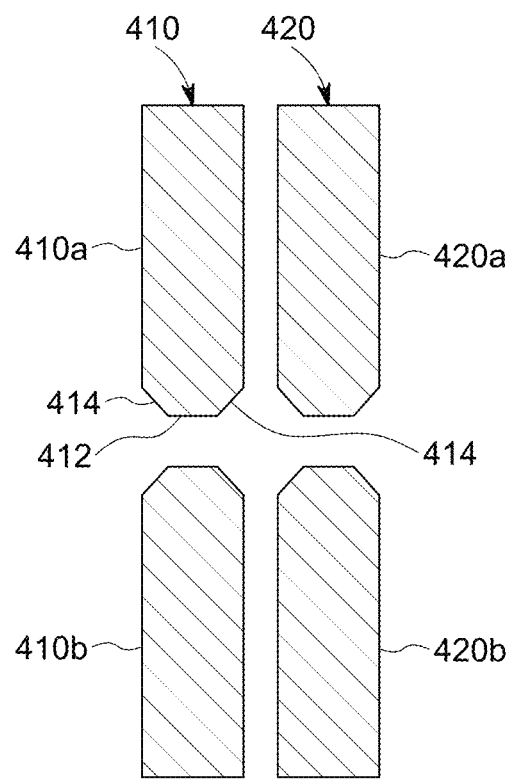
FIGS. 7A-7B depict example beam-blocking leaves according to embodiments of the disclosure.
Figure 7B:
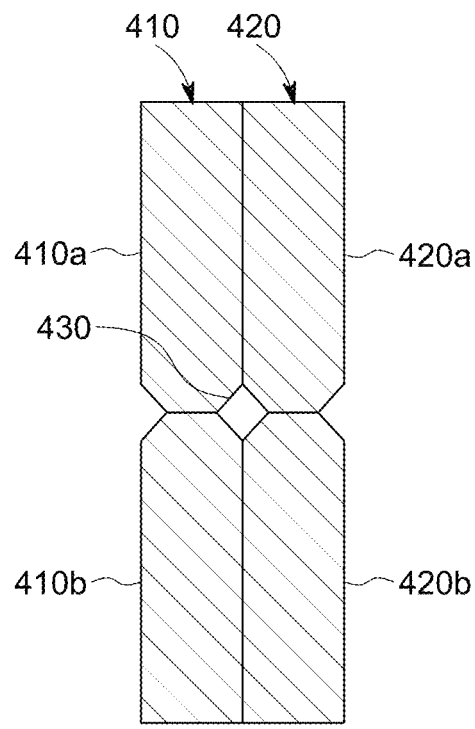

With reference to FIGS. 7A-7B, in alternative embodiments, the leaf end portions of the beam-blocking leaves of the two adjacent pairs may be configured such that the aperture formed when the two adjacent pairs of beam-blocking leaves are closed may have a rectangular or square shape in the beam's eye view. FIGS. 7A-7B show example "chamfer leaves" of two adjacent pairs 410, 420 in the beam's eye view. As shown, an example chamfer leaf may have the end portion which, in a beam's eye view, has a straight middle line section 412 orthogonal to the leaf longitudinal moving direction and beveled or angled lines sections 414 at each end of the straight middle line section 412. The term "chamfer angle" may be used herein to refer to the angle between the beveled line 414 and the straight line 412. For example, the straight middle line section 412 of the beam-blocking leaf 410a in a beam's eye view may be approximately 50% of the leaf width, and the remaining 25% at each end of the middle section 412 can be shaped in any different chamfer angles optimized for various different field slopes. The chamfer angles may range from 5-95 degrees, or from 10-90 degrees, or from 20-80 degrees, or from 40-60 degrees. In one example, the chamfer angle may be about 45 degrees. In another example, the chamfer angle may be about 60 degrees. In a specific embodiment, the beam-blocking leaf 410a may have a straight middle line section about 50% of the leaf width, with the remaining 25% at either end being beveled with a chamfer angle of about 45 or 60 degrees.

Figure 8A:
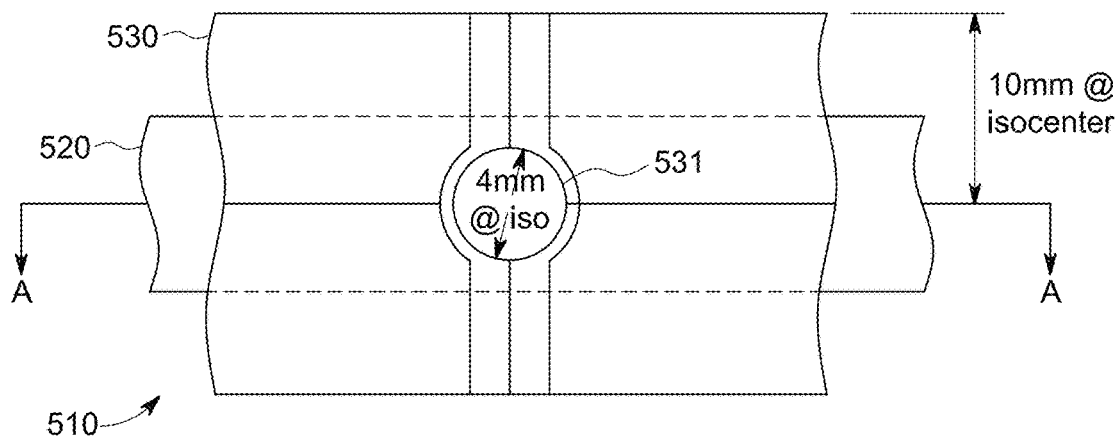
FIGS. 8A-8D depict an example multi-layer MLC according to embodiments of the disclosure.
Figure 8B:
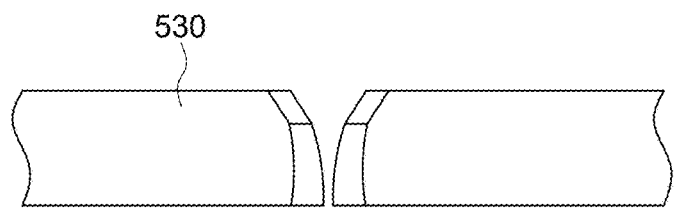

With reference to FIGS. 8A-8D, an example multi-layer MLC 510 is shown to include a distal layer or a first MLC 520 and a proximal layer or a second MLC 530. The distal layer 520 may include a pair of beam-blocking leaves each having a leaf tip profile shown in FIGS. 5A-5B ("half-moon leaf"). The other beam-blocking leaves in the distal layer 520 may have any leaf tip profiles known in the art suitable for general functionality of an MLC. The proximal layer 530 may include two adjacent pairs of beam-blocking leaves having leaf tip profiles shown in FIGS. 6A-6B ("quarter-moon leaf"). The other beam-blocking leaves in the proximal layer 530 may have any leaf tip profiles known in the art suitable for general functionality of an MLC. For clarity, only one pair of beam-blocking leaves having the leaf tip profile of FIGS. 5A-5B in the distal layer and only two adjacent pairs of beam-blocking leaves having the leaf tip profile of FIGS. 6A-6B in the proximal layer are shown in FIG. 8A. Further, it should be noted that in alternative embodiments, the pair of beam-blocking leaves having the leaf tip profile shown in FIG. 5A-5B may be arranged in the proximal layer of the multi-layer MLC, and the two adjacent pairs of beam-blocking leaves having the leaf tip profile of FIG. 6A-6B may be arranged in the distal layer of the multi-layer MLC.

With reference to FIGS. 8A-8D, the distal layer 520 and the proximal layer 530 may be arranged such that the longitudinal moving direction of the beam-blocking leaves in the distal layer 520 is generally parallel with the longitudinal moving direction of the beam-blocking leaves in the proximal layer 530. The distal layer 520 and the proximal layer 530 may be arranged such that a beam-blocking leaf in the proximal layer 530 laterally offsets a beam-blocking leaf in the distal layer 520, e.g., by about half or a third of a leaf width. According to embodiments of the disclosure, the pair of beam-blocking leaves having the leaf tip profile shown in FIGS. 5A-5B are disposed adjacent to the two adjacent pairs of beam-blocking leaves having the leaf tip profile shown in FIGS. 6A-6B. This arrangement may facilitate alignment of the aperture formed in the distal layer 520 with the aperture formed in the proximal layer 530.

Figure 8C:
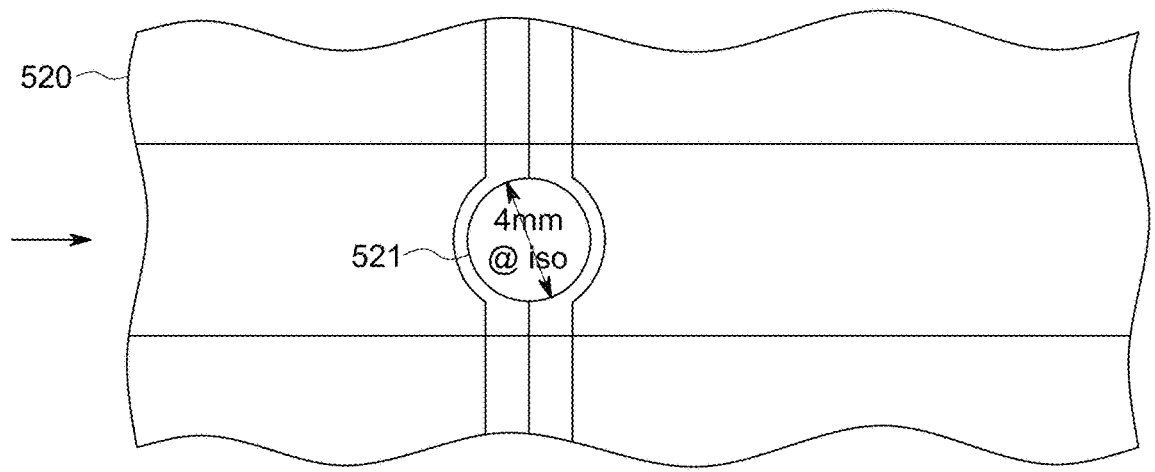
Figure 8D:
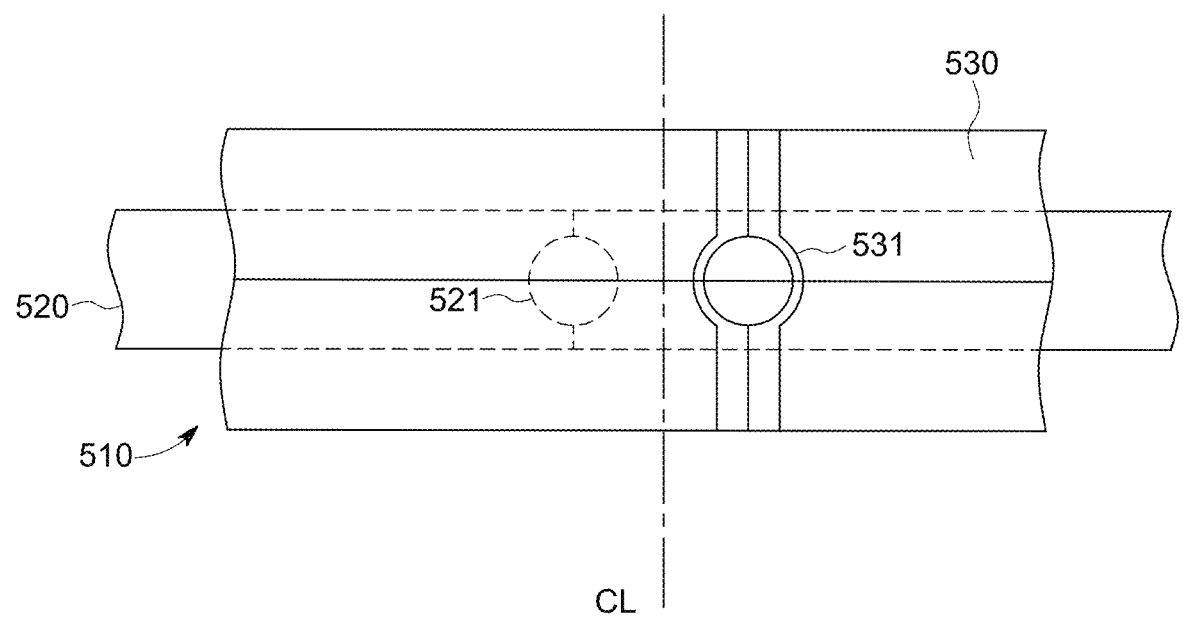

With reference to FIGS. 8A-8D, in use for SRS, all beam-blocking leaves in the distal layer 520 and the proximal layer 530 of the multi-layer MLC 510 can be closed. Because of the use of beam-blocking leaves having the leaf tip profile shown in FIGS. 5A-5B in a pair, an aperture 521 is formed by the two beam-blocking leaves of the pair in the distal layer 520, as shown in FIG. 8C. Similarly, because of the use of beam-blocking leaves having the leaf tip profile shown in FIGS. 6A-6B in two adjacent pairs, an aperture 531 is formed by the four beam-blocking leaves of the two adjacent pairs in the proximal layer 530, as shown in FIG. 8A. Therefore, when all beam-blocking leaves of the multi-layer MLC 510 are closed, the aperture 521 formed in the distal layer 520 and the aperture 531 formed in the proximal layer 530 provide a path for a thin beam to pass through, enabling SRS or radiosurgery. FIG. 8D shows an embodiment of the multi-layer MLC 510 in general use for standard treatment, where a treatment plan can be created so that the aperture 521 formed in the distal layer 520 can be blocked by the beam-blocking leaves in the proximal layer 530, and/or, the aperture 531 formed in the proximal layer 530 can be blocked by the beam-blocking leaves in the distal layer 520. The lateral-offset arrangement of the proximal layer 530 and the distal layer 520 allows the beam-blocking leaves of the distal layer 520 to block the aperture 531 formed in the proximal layer 530, and/or, the beam-blocking leaves of the proximal layer 530 to block the aperture 521 formed in the distal layer 520.

With reference to FIGS. 8A-8D, the apertures 521, 531 formed in the multi-layer MLC 510 can be aligned with the beam's central axis. By way of example, the pair of beam-blocking leaves having the leaf tip profile shown in FIGS. 5A-5B and the two adjacent pairs of beam-blocking leaves having the leaf tip profile shown in FIGS. 6A-6B can be disposed in the middle or proximate to the middle of the multi-layer MLC 510, to facilitate the alignment of the apertures with the beam's central axis and/or with the target to be treated. Alternatively, the pair of beam-blocking leaves having the leaf tip profile shown in FIGS. 5A-5B and the two adjacent pairs of beam-blocking leaves having the leaf tip profile shown in FIGS. 6A-6B can be arranged off the middle of the multi-layer MLC. The alignment of the aperture with the beam's central axis and/or with the target to be treated can also be achieved by moving a supporting structure (not shown) of the multi-layer MLC 510 relative to the source and/or by moving the patient support or couch. Therefore, the capability of aligning the apertures 521 and 531 with the beam's central axis, while preferred, is not required. The apertures 521 and 531 can be placed off the beam's central axis as long as it is within the beam divergence. A patient support or couch can be moved to align the target to be treated with the focused radiation beam passing through the aperture.

Figure 9A:
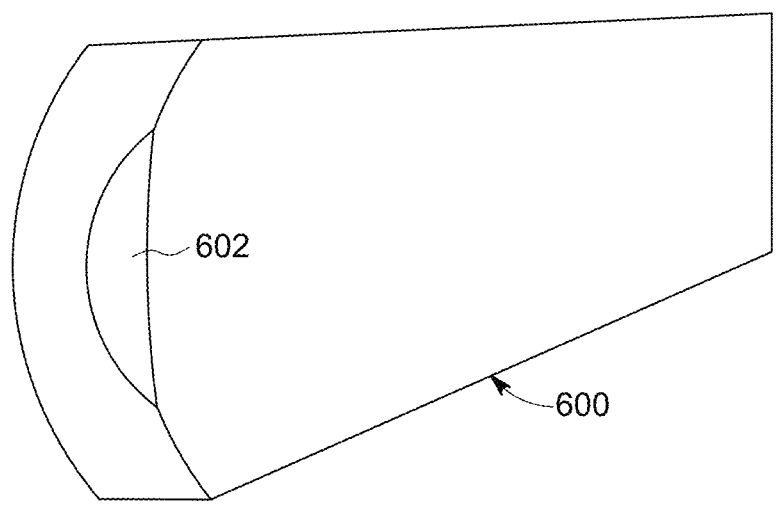
FIGS. 9A-9C depict an example beam-blocking leaf according to embodiments of the disclosure.
Figure 9B:
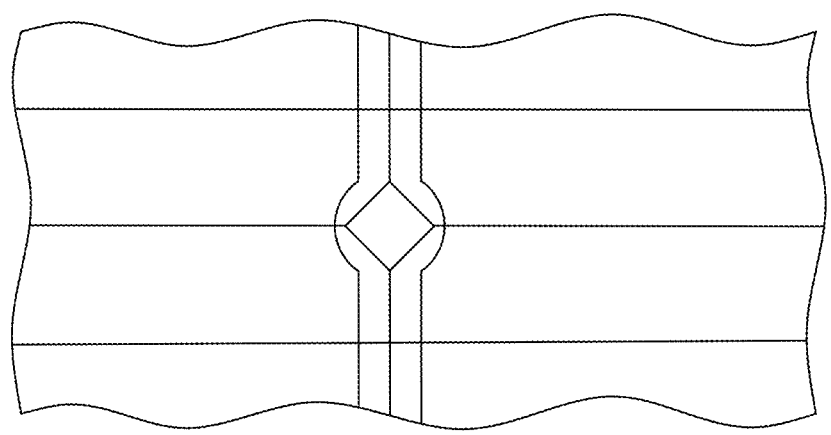
Figure 9C:
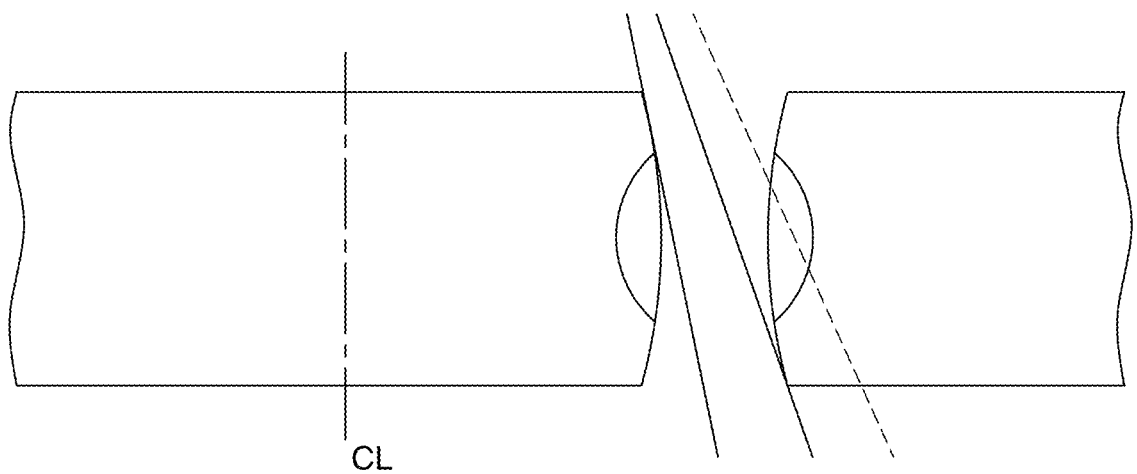

FIGS. 9A-9C show an alternative embodiment where two adjacent pairs of "chamfer leaves" having the leaf tip profile same as or similar to that shown in FIGS. 7A-7B are used in conjunction with a pair of beam-blocking leaves having the leaf tip profile same as or similar to that shown in FIGS. 5A-5B in a multi-layer MLC. FIG. 9A is an isometric view of a chamfer leaf 600 where a chamfered surface 602 is created in the end portion of the beam-blocking leaf 600. As shown, the chamfered surface 602 partially extends the height of the beam-blocking leaf 600. This may minimize or reduce the loss of shading in general use of the MLC, as shown in FIG. 9C. FIG. 9B is a beam's eye view showing an aperture formed by two adjacent pairs of chamfer leaves having the leaf tip profile shown in FIG. 9A. It will be readily recognized by one of ordinary skill in the art that the chamfered surface in the end portion of the beam-blocking leaf 600 may extend the entire height of the beam-blocking leaf.

According to embodiments of the disclosure, one of the beam-blocking leaves of the pair which have the leaf tip profile same as or similar to that shown in FIGS. 5A-5B may be additionally provided with a through-hole. Alternatively, a beam-blocking leaf other than those having the leaf tip profile same as or similar to that shown in FIGS. 5A-5B may be provided with a through-hole and operate with two adjacent pairs of beam-blocking leaves having the leaf tip profile shown in FIGS. 6A-6B or FIGS. 7A-7B. The through-hole may be shaped and sized, or configured, to allow a radiation beam to pass through for SRS. By way of example, the through-hole in the beam-blocking leaf may have a generally truncated cone shape, a generally cylindrical shape, or other regular or irregular shapes. The size of the through-hole may be different from the size of the aperture formed by the pair of beam-blocking leaves having the leaf tip profile shown in FIGS. 5A-5B, and may range from 2 to 10 millimeters, 4 to 8 millimeters, or any other dimensions generally suitable for stereotactic radiosurgery. The beam-blocking leaf provided with a through-hole may be disposed in the middle or proximate to the middle of the beam-blocking leaves of the MLC to facilitate the alignment of the through-hole with the beam's central axis. Alternatively, the beam-blocking leaf provided with a through-hole may be disposed at off the middle of the MLC. A patient support or couch can be moved to align the target to be treated with the focused radiation beam passing through the through-hole and/or the aperture of the multi-layer MLC.

FIGS. 10A-10B, 11A-11B, 12A-12B, and 13A-13B illustrate use or application of an example multi-layer MLC 710 of the disclosure in providing SRS. The example multi-layer MLC 710 shown in FIGS. 10A-10B comprises a distal layer 720 including two adjacent pairs of beam-blocking leaves having a leaf tip profile shown in FIGS. 6A-6B ("quarter-moon leaf") and a proximal layer 730 including a pair of beam-blocking leaves having a leaf tip profile shown in FIGS. 5A-5B ("half-moon leaf"). The aperture 721 formed by the selected beam-blocking leaves in the distal layer 720 and the aperture 731 formed by the selected beam-blocking leaves in the proximal layer 730 can provide a circular treatment field at the isocenter plane, with a diameter of about 4 mm for illustration purpose. The multi-layer MLC 710 can be installed in a radiation apparatus shown in FIG. 1, which allows the multi-layer MLC 710 to rotate about the beam's central axis in 360 degrees, placing the MLC 710 in various orientations relative to the patient. As such, radiation dose can be delivered to a target at the isocenter plane through the multi-layer MLC 710 at various orientations.

Figure 10A:
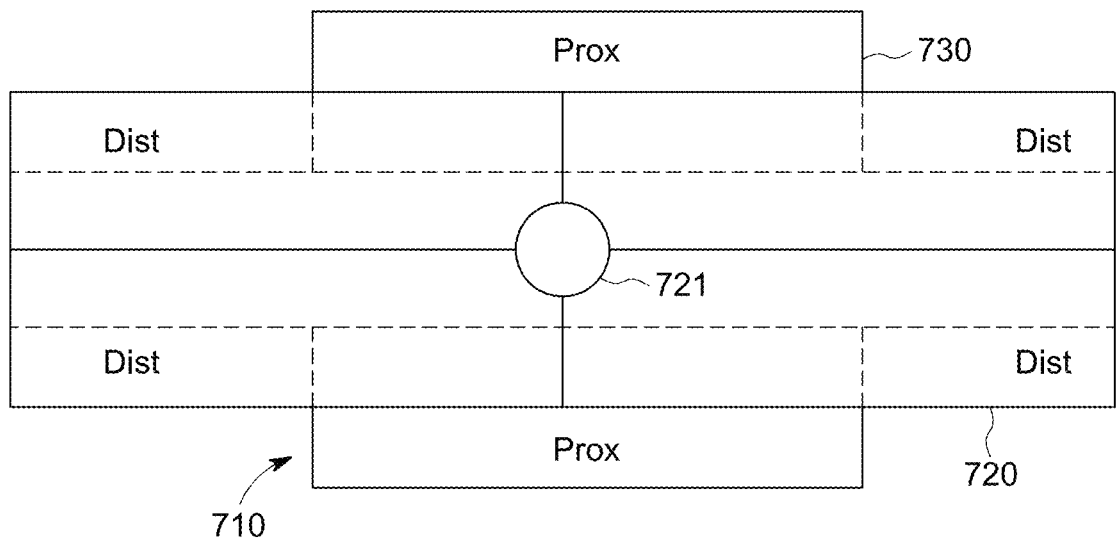
FIGS. 10A-10B depict an example multi-layer MLC according to embodiments of the disclosure.
Figure 10B:
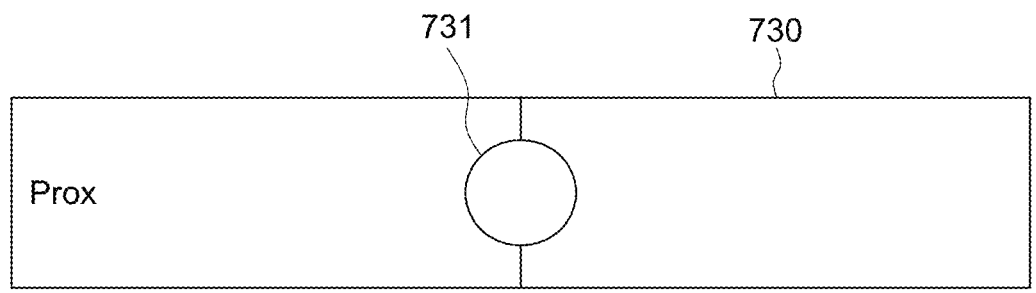
Figure 11A:
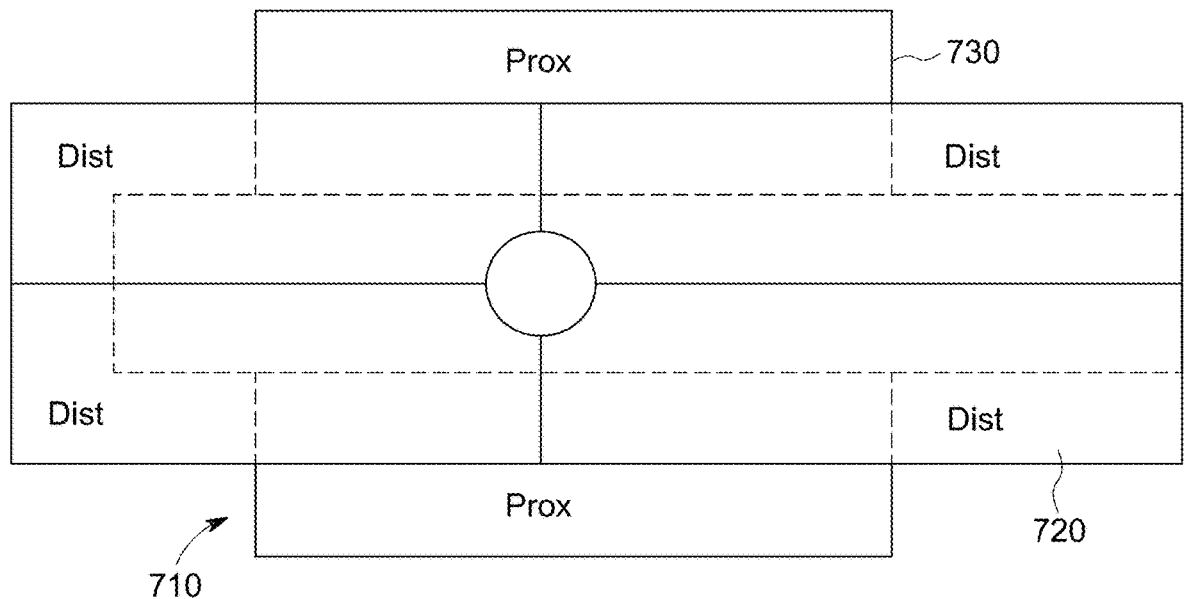
FIGS. 11A-11B, 12A-12B, and 13A-13B illustrate example uses of the multi-layer MLC shown in FIGS. 10A-10B in SRS of targets of varying sizes.
Figure 11B:
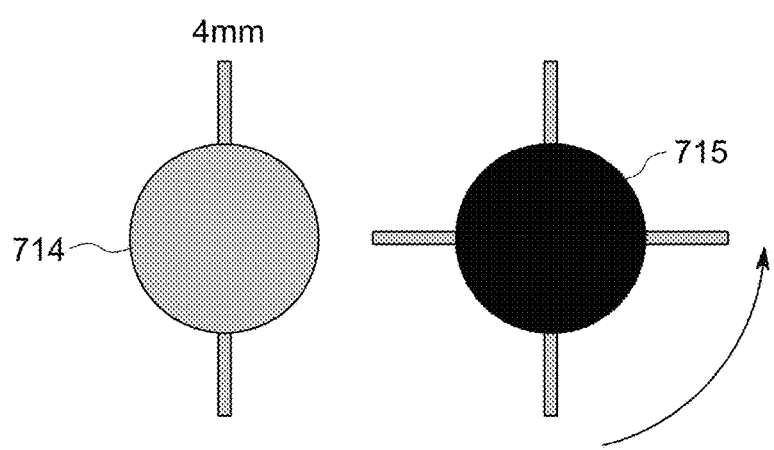
Figure 12A:
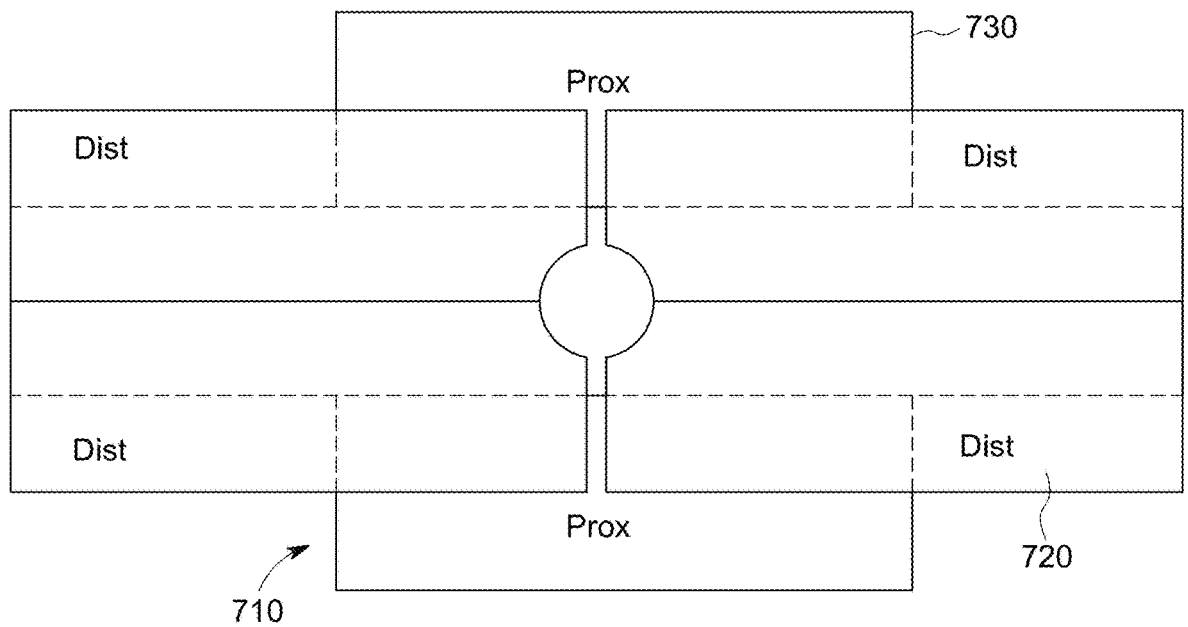
Figure 12B:
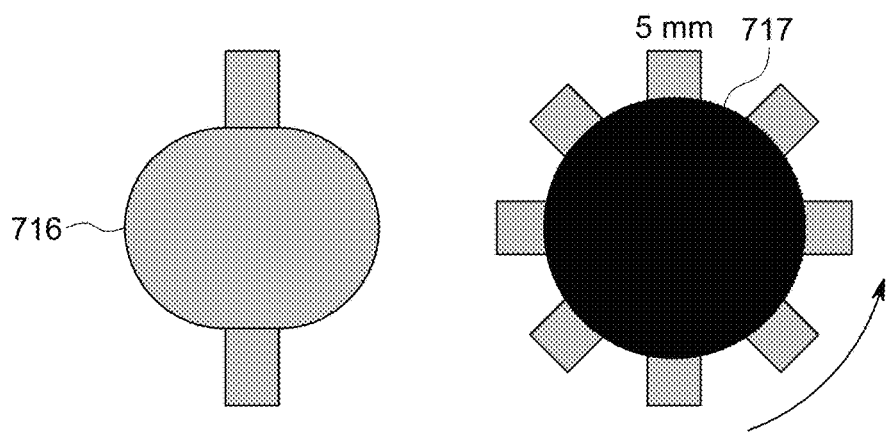
Figure 13A:
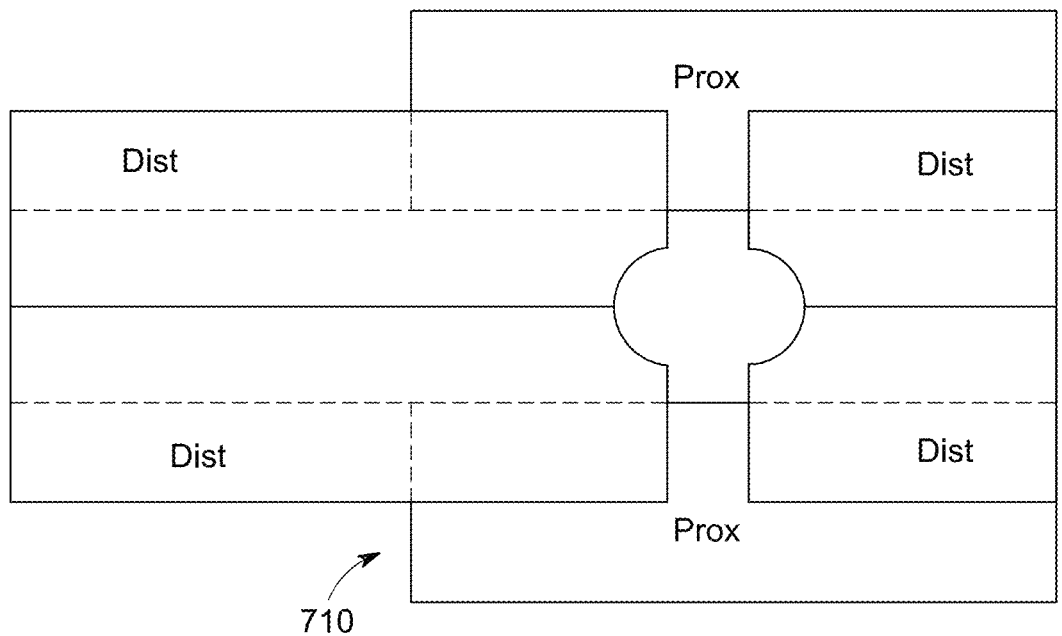
Figure 13B:
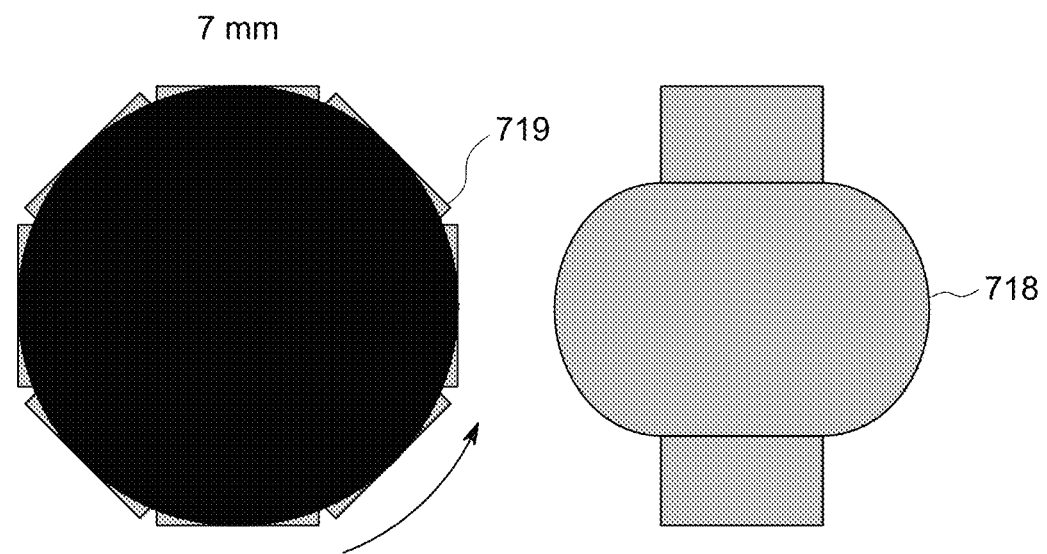

FIGS. 11A-11B, 12A-12B and 13A-13B illustrate that the same multi-layer MLC 710 shown in FIGS. 10A-10B can be used to provide SRS of targets of varying sizes. FIG. 11A illustrates that when all of the beam-blocking leaves of the multi-layer MLC 710 are closed for SRS, an aperture is formed allowing a thin beam to pass through the multi-layer MLC 710. As an example, a circular treatment field 714 having a diameter of about 4 mm is created at the isocenter plane, as shown in FIG. 11B. A rotation of the multi-layer MLC 710 about the beam's central axis allows delivery of doses to the target at various orientations of the multi-layer MLC 710, achieving a higher cumulative dose 715 to the target, as shown FIG. 11B. FIGS. 12A and 13A illustrate that the same multi-layer MLC 710 can be used for SRS of targets of larger sizes. As shown, the selected beam-blocking leaves in the distal layer 720 and the proximal layer 730 can be slightly retracted, forming a small gap between the selected beam-blocking leaves in the distal layer 720 and the proximal layer 730. The small gap increases the size of the aperture formed in the multi-layer MLC 710, resulting in forming a larger treatment field having a shape of two semicircles plus an elongate strip therebetween, as indicated at 716 in FIGS. 12B and 718 in 13B. Because the multi-layer MLC 710 can be rotated about the beam's central axis, radiation dose can be delivered to the target while the multi-layer MLC is at various orientations. As such, a higher cumulative dose of radiation can be delivered to an area of overlaps between the fields at the different orientations of the multi-layer MLC 710, as indicated at 717 in FIGS. 12B and 719 in FIG. 13B. FIG. 12B shows that an approximate circular field of a size 5 mm can be achieved by using the same multi-layer MLC 710 of FIGS. 11A-11B. FIG. 13B shows that an approximate circular field of a size 7 mm can be achieved by using the same multi-layer MLC 710 of FIGS. 11A-11B.

Various embodiments have been described with reference to the figures. It should be noted that the figures are intended to facilitate illustration and some figures are not necessarily drawn to scale. Further, in the figures and description, specific details may be set forth in order to provide a thorough understanding of the disclosure. It will be apparent to one of ordinary skill in the art that some of these specific details may not be employed to practice embodiments of the disclosure. In other instances, well known components or process steps may not be shown or described in detail in order to avoid unnecessarily obscuring embodiments of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. Further, the term "first" or "second" etc. may be used to distinguish one element from another in describing various similar elements. It should be noted the terms "first" and "second" as used herein include references to two or more than two. Further, the use of the term "first" or "second" should not be construed as in any particular order unless the context clearly dictates otherwise. Various relative terms such as "top," "bottom," "upper," "under," "higher," "lower" or similar terms may be used herein for ease of describing relative positions, directions, or spatial relationships in conjunction with the drawings. The use of the relative terms should not be construed as to imply a necessary positioning, orientation, or direction of the structures or portions thereof in manufacturing or use, and to limit the scope of the invention.

Those skilled in the art will appreciate that various other modifications may be made. All these or other variations and modifications are contemplated by the inventors and within the scope of the invention.

What is claimed is:

1. An apparatus, comprising:
a first multileaf collimator including a plurality of pairs of beam-blocking leaves each including an end portion, wherein
the end portions of a pair of beam-blocking leaves, of the plurality of pairs, are contoured to allow forming a first aperture when the beam-blocking leaves of the pair are closed,
the end portions of each leaf of the pair of beam-locking leaves include an end surface extending a height of the beam-blocking leaves of the pair of beam-locking leaves,
the end surface of each leaf includes a first rounded section, a second rounded section, and a third section between the first rounded section and the second rounded section, and
the third section includes a concave surface portion forming the first aperture when the pair of beam-locking leaves are closed.

2. The apparatus of claim 1, wherein the third section further comprises a flat surface portion on either side of the concave surface portion, the flat surface portion providing an increased contact surface when the beam-blocking leaves of the pair of beam-blocking leaves are closed to form the first aperture.

3. The apparatus of claim 2, wherein a cross-section of the third section of the end surface comprises a semi-circle shape in a beam's eye view.

4. The apparatus of claim 3, wherein the semi-circle shape has a diameter approximately a third of a width of the beam-blocking leaves of the pair of beam-blocking leaves.

5. The apparatus of claim 1, wherein the beam-blocking leaves of the pair of beam-blocking leaves are disposed in, or proximately in, a middle of the plurality of pairs of the first multileaf collimator.

6. The apparatus of claim 1, wherein the first aperture has a generally truncated cone or cylindrical shape.

7. The apparatus of claim 1, wherein the first aperture has a generally circular shape in a beam's eye view, and is configured to project a field at an isocenter plane with a field size suitable for stereotactic radiosurgery.

8. The apparatus of claim 1, wherein the first aperture has a closed shape in a beam's eye view.

9. The apparatus of claim 1, further comprising:
a second multileaf collimator including a plurality of pairs of beam-blocking leaves, wherein
the first multileaf collimator is disposed in a first level, and
the second multileaf collimator is disposed in a second level.

10. The apparatus of claim 9, wherein
the beam-blocking leaves of the first multileaf collimator are longitudinally movable in a first direction,
the beam-blocking leaves of the second multileaf collimator are longitudinally movable in a second direction that is generally parallel with the first direction, and
each of the beam-blocking leaves of the second multileaf collimator laterally offsets a beam-blocking leaf of the first multileaf collimator in a beam's eye view.

11. The apparatus of claim 10, wherein
end portions of beam-blocking leaves of two adjacent pairs of the plurality of pairs of the second multileaf collimator are contoured to allow forming a second aperture when the beam-blocking leaves of the two adjacent pairs are closed.

12. The apparatus of claim 11, wherein the beam-blocking leaves of the two adjacent pairs of the second multileaf collimator are disposed adjacent to the beam-blocking leaves of the pair of beam-blocking leaves of the first multileaf collimator such that the second aperture formed in the second multileaf collimator is generally aligned with the first aperture formed in the first multileaf collimator.

13. The apparatus of claim 12, wherein the second aperture formed in the second multileaf collimator has a closed shape in a beam's eye view.

14. The apparatus of claim 11, wherein
the end portions of the beam-blocking leaves of the two adjacent pairs of the second multileaf collimator each include an end surface extending a height of the beam-blocking leaves of the two adjacent pairs, and
the end surface includes a concave surface portion, allowing to form the second aperture when the beam-blocking leaves of the two adjacent pairs are closed.

15. The apparatus of claim 14, wherein a cross-section of the concave surface portion of the end surface of the two adjacent pairs of the second multileaf collimator includes a quarter-circle shape in a beam's eye view, thereby allowing to form the second aperture having a generally cylindrical or truncated cone shape when the beam-blocking leaves of the two adjacent pairs of the second multileaf collimator are closed.

16. The apparatus of claim 15, wherein
the end portions of the beam-blocking leaves of the pair of beam-blocking leaves of the first multileaf collimator each include an end surface extending a height of the beam-blocking leaves of the pair of beam-blocking leaves, and
the end surface of the beam-blocking leaves of the pair of beam-blocking leaves of the first multileaf collimator includes a concave surface portion, allowing to form the first aperture when the beam-blocking leaves of the pair of beam-blocking leaves are closed, wherein
a cross-section of the concave surface portion of the pair of beam-blocking leaves of the first multileaf collimator includes a semi-circle shape in the beam's eye view.

17. The apparatus of claim 16, wherein the end surface of the beam-blocking leaves of the pair of beam-blocking leaves of the first multileaf collimator further includes a flat surface portion at either side of the concave surface portion, the flat surface portion providing an increased contact surface when the beam-blocking leaves of the pair of beam-blocking leaves are closed to form the first aperture.

18. The apparatus of claim 17, wherein one of the beam-blocking leaves of the pair of beam-blocking leaves of the first multileaf collimator is provided with a through-hole, wherein the through-hole has a size different from a size of the first aperture formed by the beam-blocking leaves of the pair of beam-blocking leaves of the first multileaf collimator.

* * * * *